United States Patent [19]

Adelstein

[11] 4,003,904
[45] * Jan. 18, 1977

[54] ANTI-DIARRHEAL OXADIAZOLES
[75] Inventor: Gilbert W. Adelstein, Evanston, Ill.
[73] Assignee: G. D. Searle & Co., Chicago, Ill.
[ * ] Notice: The portion of the term of this patent subsequent to Nov. 4, 1992, has been disclaimed.
[22] Filed: Apr. 16, 1975
[21] Appl. No.: 568,694

Related U.S. Application Data
[63] Continuation-in-part of Ser. No. 456,755, April 1, 1974, Pat. No. 3,917,615.

[30] Foreign Application Priority Data
Feb. 26, 1975 South Africa .................... 75/1193
Mar. 26, 1975 Greece .................... 6337

[52] U.S. Cl. .................... 260/293.54; 260/247.5 R; 260/293.67; 260/296 R; 260/296 B; 260/307 G; 260/308 D; 424/248.4; 424/263; 424/267; 424/269; 424/248.57
[51] Int. Cl.$^2$ .................... C07D 85/54
[58] Field of Search .................... 260/293.54, 247.5 E, 260/293.67, 307 G, 296 R, 296 B

[56] References Cited
UNITED STATES PATENTS

| | | | |
|---|---|---|---|
| 3,141,019 | 7/1964 | Palazzo et al. | 260/247.5 |
| 3,299,044 | 1/1967 | Cusic et al. | 260/239 |
| 3,502,668 | 3/1970 | Palazzo et al. | 260/247.5 |
| 3,585,209 | 6/1971 | Derappe | 260/307 |
| 3,655,684 | 4/1972 | Osbond et al. | 260/307 G |
| 3,720,685 | 3/1973 | Breuer et al. | 260/307 G |
| 3,917,615 | 11/1975 | Adelstein | 260/293.54 |

Primary Examiner—Henry R. Jiles
Assistant Examiner—C. M. S. Jaisle
Attorney, Agent, or Firm—John J. McDonnell

[57] ABSTRACT

The present invention encompasses a compound of the formula

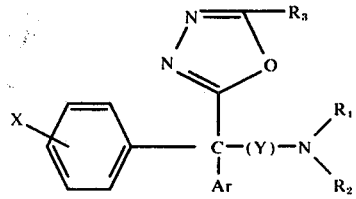

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula

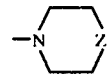

wherein Z is oxygen, methylene, phenylhydroxymethylene, phenylcarboxymethylene or, phenylloweralkoxymethylene, or an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms, or loweralkoxy having 1–7 carbon atoms when $R_3$ is hydrogen or Ar is 3 or 4 pyridyl when $R_3$ is lower alkyl having 1–7 carbon atoms.

The compounds of the present invention are prepared by converting the corresponding nitriles to 1H-tetrazoles and in turn reacting the 1H-tetrazole with ethyl chloroglyoxylate, hydrolyzing the resulting ester to the acid and decarboxylation to provide compounds wherein $R_3$ is hydrogen. Compounds of the present invention are anti diarrheal agents.

15 Claims, No Drawings

ANTI-DIARRHEAL OXADIAZOLES

This is a continuation-in-part of my copending application Ser. No. 456,755, filed Apr. 1, 1974, now U.S. Pat. No. 3,917,615.

The present invention encompasses a compound of the formula

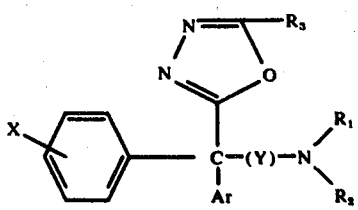

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula

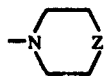

wherein Z is oxygen, methylene, phenylhydroxymethylene, phenylcarboxymethylene or, phenylloweralkoxymethylene, or an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms, or loweralkoxy having 1–7 carbon atoms when $R_3$ is hydrogen or Ar is 3 or 4 pyridyl when $R_3$ is lower alkyl having 1–7 carbon atoms.

Alkylene refers to methylene, ethylene, propylene, isopropylene, butylene and similar radicals. Halo refers to fluoro, chloro, bromo, and iodo. Loweralkyl refers to methyl, ethyl, propyl, isopropyl, butyl, pentyl, hexyl, heptyl and similar radicals. Loweralkoxy refers to methoxy, ethoxy, propoxy, butoxy, pentoxy, hexoxy, heptoxy and the like.

Azamonocyclic ring of the formula

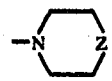

includes ring systems such as piperidino, morpholino, 4-hydroxy-4-phenylpiperidino, 4-phenyl-4-carboxypiperidino and esters thereof.

Azabicycloalkane structures having 6–9 carbon atoms include radicals such as 2-azabicyclo[2.2.2]oct-2-yl, 3-azabicyclo[3.2.2]non-3-yl, 6-azabicyclo[3.2.1]oct-6-yl, 8-azabicyclo[4.3.0]non-8-yl, 7-azabicyclo[2.2.1]hept-7-yl and similar radicals. An embodiment of the present invention is represented by a compound of the formula

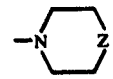

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula

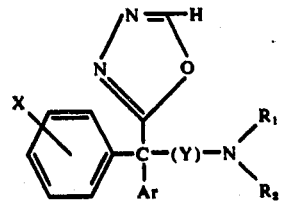

wherein Z is oxygen, methylene, phenylhydroxymethylene or, phenylcarboxymethylene, phenylloweralkoxymethylene, or an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms; or loweralkoxy having 1–7 carbon atoms.

A further embodiment of the present invention is represented by a compound of the formula

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula wherein Z in oxygen, methylene, phenylhydroxymethylene, phenylcarboxymethylene or, phenylloweralkoxymethylene, X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms, or loweralkoxy having 1–7 carbon atoms.

A further embodiment of the present invention is represented by a compound of the formula

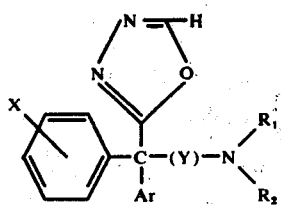

and the pharmaceutically acceptable acid addition salts thereof wherein Y is alkylene having 1–4 carbon atoms; $R_1$ and $R_2$ together with N is a heterocyclic ring system consisting of an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms, or loweralkoxy having 1–7 carbon atoms.

A compound of the formula

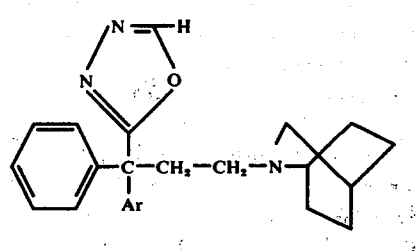

and the pharmaceutically acceptable acid addition salts thereof wherein Ar is phenyl or pyridyl is a preferred embodiment. Compounds of the formula

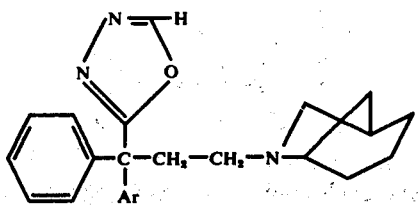

and the pharmaceutically acceptable acid addition salts thereof wherein Ar is phenyl or pyridyl are also preferred. An embodiment of the present invention is represented by a compound of the formula

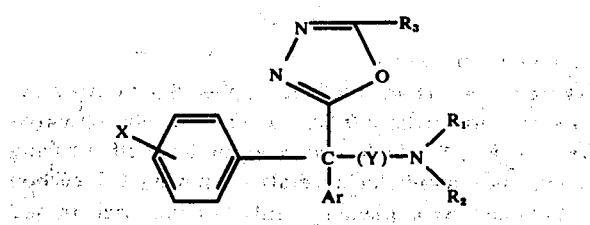

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula

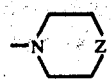

wherein Z in oxygen, methylene, phenylhydroxymethylene, phenylcarboxymethylene or, phenylloweralkoxymethylene, or an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; Ar is 3 or 4 pyridyl; $R_3$ is loweralkyl having 1–7 carbon atoms.

A further embodiment of the present invention is represented by a compound of the formula

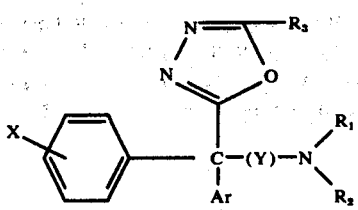

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula

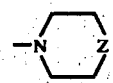

wherein Z is oxygen, methylene, phenylhydroxymethylene, phenylcarboxymethylene, or phenylloweralkoxymethylene, X is hydrogen, halogen, loweralkyl having 1–7 carbon atoms, or loweralkoxy having 107 carbon atoms; Ar is 3 or 4 pyridyl; and $R_3$ is lower alkyl having 1–7 carbon atoms.

Still a further embodiment of the present invention is represented by a compound of the formula

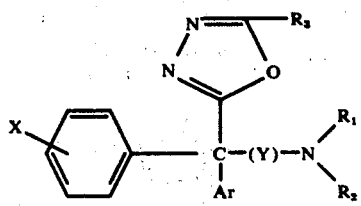

and the pharmaceutically acceptable acid addition salts thereof wherein Y is alkylene having 1–4 carbon atoms; $R_1$ and $R_2$ together with N is a heterocyclic ring system consisting of an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; Ar is 3 or 4 pyridyl; and $R_3$ is lower alkyl having 1–7 carbon atoms.

Compounds of the formula

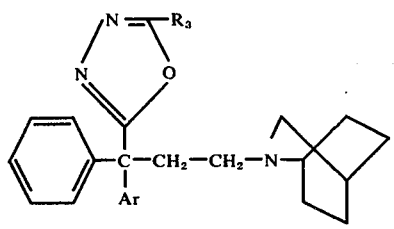

and the pharmaceutically acceptable acid addition salts thereof wherein Ar is 3 or 4 pyridyl and $R_3$ is loweralkyl are preferred in that they are potent anti-diarrheal agents which lack central nervous system affecting properties. 5-[1-Phenyl-1-(3-pyridyl)-3-(2-azabicyclo[2.2.2]oct-2-yl)propyl]-2-methyl-1,3,4-oxadiazole and 5-[1-phenyl-1-(4-pyridyl)-3-(2-azabicyclo[2.2.2]oct-2-yl)propyl]-2-methyl-1,3,4-oxadiazole are especially preferred.

Replacement of the 2-azabicyclo 2.2.2]oct-2-yl radical with 6-azabicyclo[3.2.1]oct-6-yl radical in the above formula also provides a preferred embodiment which is exemplified by 4-[1-phenyl-1-(3-pyridyl)-3-(6-azabicyclo[3.2.1]oct-6-yl)propyl]-2-methyl-1,3,4-oxadiazole.

Methods for preparing nitrile precursors are described in U.S. Pat. No. 3,299,044 and include the reaction of an appropriate amine with a a halide of the formula

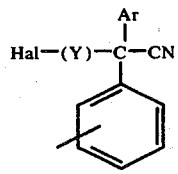

wherein Y, Ar, X are as above and Hal is chlorine or bromine. Alternately, the nitriles can be prepared by the reaction of a diarylacetonitrile of the formula

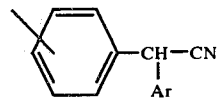

first with sodamide and then with an alkyl halide of the formula

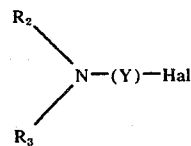

wherein $R_1$, $R_2$, X, Y, Ar, and Hal are previously described.

1,1-Phenyl substituted amino substituted alkyl nitriles suitable for practicing this invention are described in U.S. Pat. Nos. 3,497,519, 2,841,589, 3,299,044, 2,823,233, 3,225,054 and 3,318,869 and an article by R. Moffett and B. Aspergran, *J. Amer. Chem. Soc.*, 79, 4451 (1957). As shown in Scheme A, treatment of the nitrile with azide ion by methods similar to those described by G. Moersch and D. Morrow, *J. Med. Chem.*, 10, 149 (1967) provides the corresponding tetrazole.

The tetrazole intermediates are converted to the corresponding 1,3,4-oxadiazole by treatment with an acid anhydride following the procedures substantially as described by R. Huisgen et al., *Chem. Ber.*, 93, 2106 (1960).

Compounds of the present invention wherein $R_3$ is hydrogen are prepared by the reaction sequence set out in scheme I

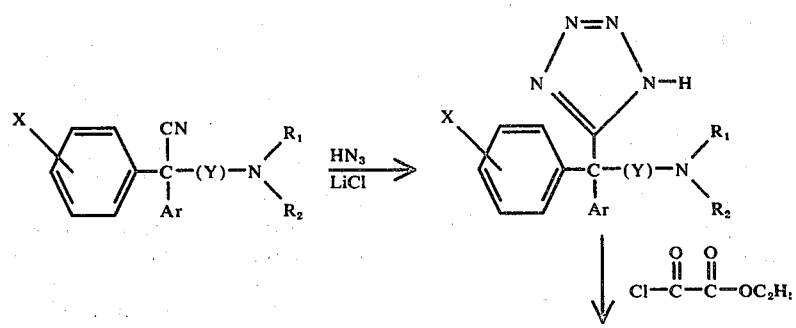

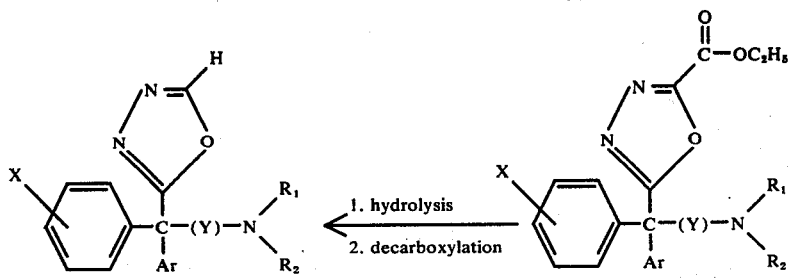

Scheme I

Thus 2,2-diphenyl-4-(2-azabicyclo[2.2.2]oct-2-yl)butyronitrile described in U.S. Pat. No. 3,318,869 is reacted with sodium azide in DMF to provide 5-[1,1-diphenyl-3-(2-azabicyclo[2.2.2]oct-2-yl)propyl]-1H-tetrazole. This tetrazole is reacted with ethyl chloroglyoxylate in pyridine at −6° C to provide ethyl [1,1-diphenyl-3-(2-azabicyclo[2.2.2]oct-2-yl)propyl]-1,3,4-oxadiazole-2-carboxylate hydrochloride. This ester is hydrolysed in aqueous potassium hydroxide to provide 5-[1,1-diphenyl-3-(2-azabicyclo[2.2.2]oct-2-yl)propyl]-1,3,4-oxadiazole-2-carboxylic acid. Heating this acid for 15 minutes in an oil bath at 130°–140° provides 5-[1,1-diphenyl-3-(2-azabicyclo[2.2.2]oct-2-yl)propyl]-1,3,4-oxadiazole. The hydrochloride salt melts at 233°–234.5° C.

α-Phenyl-3-pyridylacetonitrile (U.S. Pat. No. 3,225,054) is reacted with 2-(2-chloroethyl)-2-azabicyclo[2.2.2]octane in toluene to provide 2-phenyl-2-(3-pyridyl)-4-(2-azabicyclo[2.2.2]oct-2-yl)butyronitrile. This nitrile is reacted with sodium azide in DMF containing lithium chloride to provide 5-[1-phenyl-1-(3-pyridyl)-3-(2-azabicyclo[2.2.2]oct-2-yl)propyl]-1H-tetrazole. Reaction this tetrazole with acetic anhydride in pyridine provides 5-[1-phenyl-1-(3-pyridyl)-3-(2-azabicyclo[2.2.2]oct-2-yl)propyl]-2-methyl-1,3,4-oxadiazole, the oxalate salt melts at 171°–172° C.

The anti-diarrheal properties of the compounds of the present invention are shown by the following test.

CHARCOAL MEAL TEST

Mice weighing 18–24 grams and previously fasted for 24 hours are each given orally 0.2 ml. of a suspension containing 10% charcoal and 1% methylcellulose. The test compounds are administered intragastrically 1 hour prior to the charcoal meal. 3.5 Hours after administration of the meal the mice are sacrificed by cervicle dislocation and the cecum is examined for the presence or absence of charcoal on an all or none basis. Each compound is tested at three dose levels (typically 30, 10, 3 mg/kg) in groups of 6 mice per dose level. Control groups of mice given saline only were run concurrently with each test group.

CASTOR OIL INDUCED DIARRHEA TEST

Following the experimental design of Niemegear et al. Arzniem - Forsch 22: 515–518 (1972). Adult male Charles River rats weighting 180–200 grams in groups of 12 are fasted in community cages for 24 hours prior to the test with free access to water. The test compounds were in 0.5% methyl cellulose suspension at 2.0 ml/kg. The control constitutes the vehicle only. One hour after the compound administration, 1.0 m. of castor-oil was given to each rat intragastrically. The rats were then observed for the presence or absence of diarrhea at hourly intervals for up to 8 hours, post administration of castor-oil. The median effective dose value (ED50) was calculated using the method of Berkson, J. Amer. Statist. Assoc. 48 565–99 (1953). Lack of central nervous system effective properties are shown by the following test.

MOUSE HOT PLATE TEST

A mouse (adult male weighing 18–25 grams) is placed in a restraining cylinder on a hot plate with the temperature controlled at 55° ± 0.3° C. The reaction time of the mouse to lick a foot or jump is measured at 60, 40 and 20 minutes before and 30, 60, 90, and 120 minutes after administration of the test compound. The "normal" reaction time is measured as the median of the three pretreatment reaction times. A positive response consist of a reaction time greater than twice the normal time at any of the post treatment times. A dose (50 mg/kg administered intraperitoneally) of the test compound is considered active when 50 per cent or more of the animals used show a positive response.

TAIL CLIP TEST

A special clip is applied to the base of the tail of the mouse (adult male weighing 18–25 grams) and the time for the animal to turn around to bite at it is measured. The sensitivity of each mouse is determined one-half hour prior to drug administration. Only those mice attempting to bite the clip are included in the experiment. The test compound is then administered intrapertitoneally and the response to placement of the clip is determined at 30, 60, 90, and 120 minutes after treatment. A response is considered positive if the animal takes more than 2 times the pre-drug time to bite at the clip at any of these time intervals. A test compound is considered active when 50 per cent or more of the animals used show a positive response.

The compounds herein described can be combined with pharmaceutically acceptable carriers to provide novel pharmaceutical compositions. The concentration of active ingredient in the composition is not critical, but is preferably 1–80%. These compositions can be administered orally, suitable forms for such administration including tablets, lozenges, capsules, dragees, pills, powders. solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin; talc; calcium phosphates such as dicalcium phosphate or tricalcium phosphate; sodium sulfate; calcium sulfate; polyvinyl pyrrolidone; acacia; polyvinyl alcohol; stearic acid; alkaline earth metal stearates such as magnesium stearate; oils such as peanut oil, cottonseed oil, sesame oil; olive oil, corn oil, oil of theobroma; water; agar; alginic acid; and benzyl alcohol, as well as other non-toxic compatible substances used in pharmaceutical formulations The compounds of this invention can be used to produce an antidiarrheal effect in mammals by administering the instant novel compositions containing a therapeutically effective amount of the active ingredient. The term "therapeutically effective amount" is defined as the amount of active ingredient that will produce an antidiarrheal effect, i.e. which will reverse, inhibit or prevent diarrhea. For a particular subject, the amount of active ingredient to be used will vary with the subject involved, the severity of the diarrhea, and the particular active ingredient used. The therapeutically effective amount of a particular active ingredient can be determined by comparing its potency to that of a known standard, for which the therapeutic dosage is known. Typically 0.1–25 mg/kg is an effective antidiarrheal amount of a given compound.

Those skilled in the art will recognize that observations of activity in standardized tests for particular biological effects are fundamental to the development of valuable new drugs, both veterinary and human.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade (° C.).

EXAMPLE 1

26.3 Parts of 2,2-diphenyl-4-(2-azabicyclo[2.2.2]oct-2-yl)butyronitrile described in U.S. Pat. No. 3,318,869 is dissolved in 60 parts by volume of dimethylformamide along with 9.0 parts of sodium azide. 7.4 parts of ammonium chloride and 0.12 part of lithium chloride and refluxed for 12 hours. Upon reflux a solid separates which is 4-[1,1-diphenyl-3-(2-azabicyclo[2.2.2]oct-2-yl)propyl]-1H-tetrazole.

1.6 Parts by volume ethyl chloroglyoxylate was added to a stirred suspension of 5-[1,1-diphenyl-3-(2-azabicyclo[2.2.2]oct-2-yl)propyl]-1H-tetrazole in pyridine. After the reaction mixture was stirred for 15 minutes at −6° C, it was heated with stirring to 60° and kept at that temperature for about 2 hours. The reaction mixture was then cooled and stripped to give a residue which was dissolved in water. Treatment of the solution with excess potassium carbonate in water gave a solid. This solid was dissolved in ether. The ether solution was washed with water, dried over sodium sulfate, treated with charcoal and filtered. The filtrates were stripped in vacuum to give a brown gum. This gum was dissolved in ethanol and treated with excess hydrogen chloride. The precipitate which formed was filtered off, washed with a mixture of ethanol and ether and air-dried. This procedure provided ethyl-5-[1,1-diphenyl-3-(2-azabicyclo[2.2.2]oct-2-yl)propyl]1,3,4-oxadiazole-2-carboxylate hydrochloride which melted at 198.0°–200° C.

8.0 Parts of the above oxadiazole was suspended in 200 parts by volume of 5% sodium hydroxide. This suspension was heated to reflux temperature for five minutes. Upon cooling the solution to room temperature, a gum precipitated. This gum was dissolved in water. The resultant solution was extracted with ether. Adjustment of the aqueous phase of the extraction to pH 6 gave a gum. This gum was extracted several times with methylene chloride and the extracts were combined and then stripped in vacuum to give a solid. The solid now was taken up in methylene chloride. The resultant solution was filtered. The filtrates were concentrated to a lower volume. Dilution of these filtrates with methanol caused the formation of a solid material. This solid material was filtered off, washed with an ether/methanol mixture and dried to give 5-[1,1-diphenyl-3-(2-azabicyclo[2.2.2]oct-2-yl)propyl]-1,3,4-oxadiazole-2-carboxylic acid hydrate, melting at about 128°–129° C.

3.1 Parts of the above oxadiazole was heated in an oil bath for fifteen minutes during which time the oxadiazole melted and gave off gas. The glass which resulted from this procedure was extracted with ether. The extracts were then stripped in vacuum. The gum which resulted was treated with excess hydrogen chloride in 2-propanol and cooled to 0°. The precipitate which formed was filtered off, washed with acetone and dried in vacuum to give 5-[1,1-diphenyl-3-(2-azabicyclo[2.2.2]oct-2-yl)propyl]-1,3,4-oxadiazole hydrochloride melting at 233°–234.5° C. This compound has the following structural formula

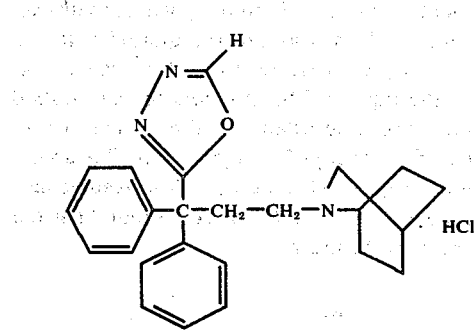

This salt is dissolved in dilute sodium bicarbonate solution and the free base is extracted with ether. The ethereal extracts are dried over anhydrous potassium carbonate, filtered, and the solvent is removed to provide 5-[1,1-diphenyl-3-(2-azabicyclo[2.2.2]oct-2-yl)propyl]-1,3,4-oxadiazole.

EXAMPLE 2

A mixture of 25 parts of benzyl cyanide, 35 parts of 3-bromopyridine and 220 parts of dry toluene is heated to 80° C. with stirring. Then, 19 parts of sodamide is added portionwise over a period of 1 hour while the temperature is maintained at 80°–85° C. with some cooling. The resultant mixture is heated to 105° C. and a solution of 56 parts of 2-(2-chloroethyl)-2-azabicyclo[2.2.2]octane in 220 parts of dry toluene is added portionwise. The mixture is then heated at 105°–110° C. for an additional 3 hours before it is cooled and 250 parts of water is added. The organic layer is separated and dried and the solvent is evaporated to leave a residue which is dissolved in ether and filtered. The ether solvent is evaporated from the filtrate and the residual oil is distilled under reduced pressure to provide 2-phenyl-2-(3-pyridyl)-4-(2-azabicyclo[2.2.2]oct-2-yl)butyronitrile. Alternately α-phenyl-3-pyridylacetonitrile (U.S. Pat. No. 3,225,054) is reacted with 2-(2-chloroethyl)-2-azabicyclo[2.2.2]octane directly.

A mixture of 5.69 parts of 2-phenyl-(3-pyridyl)-4-(2-azabicyclo[2.2.2]oct-2-yl)butyronitrile, 1.67 parts of sodium azide, 1.38 parts of ammonium chloride and 0.025 parts of lithium chloride in 30 parts by volume of dimethylformamide was stirred for 12 hours under nitrogen at 120° C. After the reaction time was completed, the material was cooled and filtered. The collected precipitate was washed with dimethylformamide and water. The precipitate was then dissolved in 100 parts by volume of 0.2N NaOH. The resultant solution was filtered. The filtrates were neutralized with dilute hydrochloric acid. The product which separated was recrystallized from ethanol. The procedure afforded 5-[1-phenyl-1-(3-pyridyl)-3-(2-azabicyclo[2.2.2]oct-2-yl)propyl]-1H-tetrazole.

2.0 Parts of 5-[1-phenyl-1-(3-pyridyl)-3-(2-azabicyclo[2.2.2]oct-2-yl)propyl]-1H-tetrazole was reacted with 4.0 parts of acetic anhydride in pyridine and refluxed for 2 hours to provide 5-[1-phenyl-1-(3-pyridyl)-3-(2-azabicyclo[2.2.2]oct-2-yl)propyl]-2-methyl-1,3,4-oxadiazole.

0.54 Parts of the above oxadiazole was combined with 0.215 parts of oxalic acid in 6.0 parts of methanol to give a solution. This solution was diluted with 6.0 parts of ether to give a white precipitate which was filtered from the liquors. This precipitate was washed with methanol-ether and ether and then dried in vacuum to give 5-[1-phenyl-1-(3-pyridyl)-3-(2-azabicyclo[2.2.2]oct-2-yl)propyl]-2-methyl-1,3,4-oxadiazole oxalate melting at 171°–172° C. This compound has the following structural formula

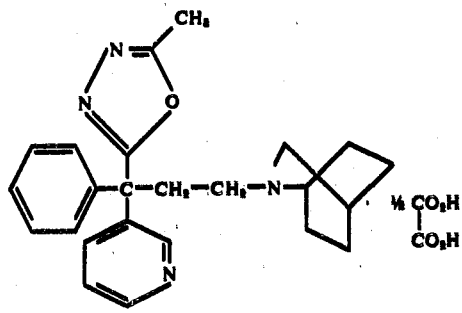

EXAMPLE 3

Following the procedure set out in Example 1 and using equivalent quantities, 5-[1-phenyl-1-(3-pyridyl)-(2-azabicyclo[2.2.2]oct-2-yl)propyl]-1-tetrazole (from Example 2) is converted to 5-[1-phenyl-1-(3-pyridyl)-3-(2-azabicyclo[2.2.2]oct-2-yl)propyl]-1,3,4-oxadiazole, having the following structural formula

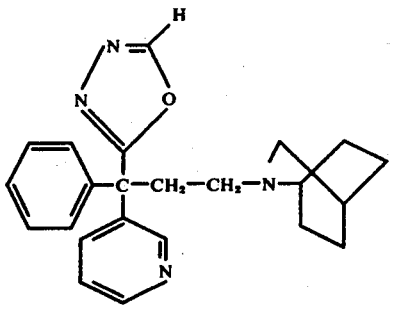

EXAMPLE 4

Following the procedure set out in Example 1 and using equivalent quantities 2-phenyl-2-(2-pyridyl)-5-(3-azabicyclo[3.2.2]non-3-yl)valeronitrile (U.S. Pat. No. 3,318,869) is converted to 5-[1-phenyl-1-(2-pyridyl)-4-(3-azabicyclo[3.2.2]non-3-yl)butyl]-1,3,4-oxadiazole, having the following structural formula

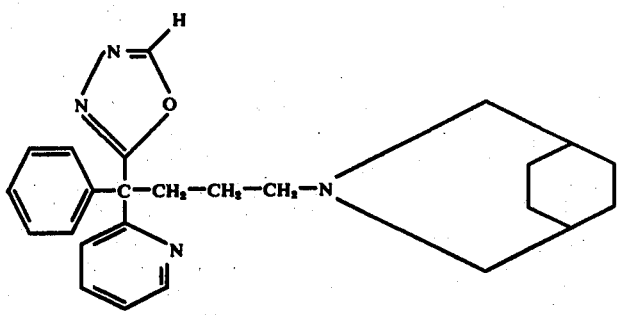

EXAMPLE 5

Substituting an equivalent quantity of 4-bromopyridine for 3-bromopyridine and following the procedure set out in Example 2 provides 4-[1-phenyl-1-(4-pyridyl)-3-(2-azabicyclo[2.2.2]oct-2-yl)propyl]-1H tetrazole and following the procedures set out in Example 1 this tetrazole is converted to 5-[1-phenyl-1-(4-pyridyl)-3-(2-azabicyclo[2.2.2]oct-2-yl)propyl]-1,3,4-oxadiazole, having the following structural formula

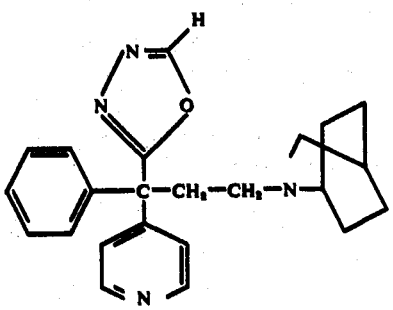

EXAMPLE 6

Following the procedure set out in Example 1 and using equivalent quantities 2,2-diphenyl-4(2-azabicyclo-[2.2.2]oct-2-yl)butyronitrile described in U.S. Pat. No. 3,318,869 is converted to 5-[1,1-diphenyl-3-(6-azabicyclo[3.2.1]oct-6-yl)propyl]-1H-tetrazole which in turn is converted to 5-[1,1-diphenyl-3-(6-azabicyclo[3.2.1]oct-6-yl)propyl]-1,3,4-oxadiazole having the following structural formula

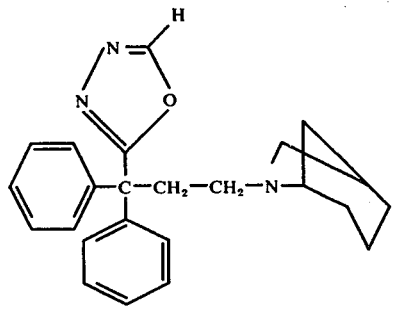

EXAMPLe 7

Following the procedure set out in Example 1 and using equivalent quantities 2,2-diphenyl-4-(8-azabicyclo[4.3.0]non-8yl)butyronitrile described in U.S. Pat. No. 3,318,869 is converted to 5-[1,1-diphenyl-3-(8-azabicyclo[4.3.0]non-8-yl)propyl]-1,3,4-oxadiazole having the following structural formula

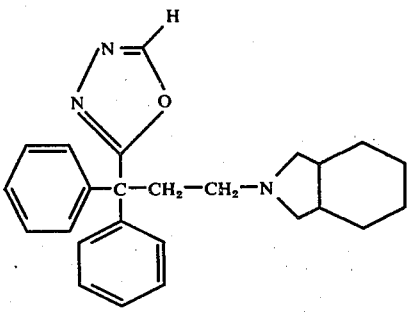

EXAMPLE 8

15 Parts of 2,2-diphenyl-4-bromobutyronitrile are condensed with 12.9 parts of 7-azabicyclo[2.2.1]heptane by reflux in 100 parts by volume of ethylene glycol monomethyl ether. The reaction mixture is cooled and extracted with dilute hydrochloric acid. The aqueous hydrochloric acid extract is made basic with sodium hydroxide solution and extracted with ether. The ether extracts are dried over anhydrous sodium sulfate. Filtration and removal of the ether by evaporation at reduced pressure provides 2,2-diphenyl-4-(7-azabycyclo[2.2.1]hept-7-yl)butyronitrile, melting at 79°-81°. 4.9 Parts of this butyronitrile, 1.5 parts of sodium azide, 1.2 parts of ammonium chloride, and 0.023 part of lithium chloride are placed in 50 parts by volume of dimethylformamide and heated at 125° for 12 hours. The mixture is cooled and the solid is filtered from the dimethylformamide. The solid is washed with dimethylformamide and water. The dried solid is 5-[1,1-diphenyl-3-(7-azabicyclo[2.2.1]hept-7-yl)propyl]-1H-tetrazole, melting at 284°-286°.

Following the procedure set out in Example 1 and using equivalent quantities this tetrazole is converted to 5-[1,1-diphenyl-3-(7-azabicyclo[2.2.1]hept-7-yl)propyl]-1,3,4-oxadiazole, having the following structural formula

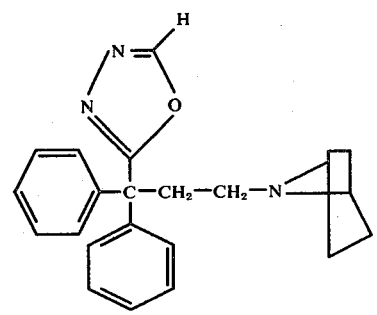

EXAMPLE 9

15 Parts of 2,2-diphenyl-4-bromobutyronitrile, 8.9 parts of 4-hydroxy-4-phenylpiperidine and 400 parts by volume of ethylene glycol monomethyl ether are heated together at reflux for 18 hours under nitrogen. The solution is cooled and the volume is reduced 50% at 60° under reduced pressure. The concentrated mixture is diluted with 1200 parts of water, made basic with sodium hydroxide, and then extracted with ether. The product is isolated from ether by extraction into acid solution followed by making the solution basic and extracting with ether. The dried product is 2,2-diphenyl-4-(4-hydroxy-4-phenyl)piperidinobutyronitrile, melting at 221°-223°.

8.0 Parts of this nitrile, 2.0 parts of sodium azide, 1.6 parts ammonium chloride, 0.030 part of lithium chloride and 20 parts by volume of dimethylformamide are by the method of Example 1 converted to 5-[1,1-diphenyl-3-(4-hydroxy-4-phenyl)piperidino]propyl-1H-tetrazole which in turn is converted to 5-[1,1-diphenyl-3-(4-hydroxy-4-phenyl)piperidino[propyl-1,3,4-oxadiazole having the following structural formula

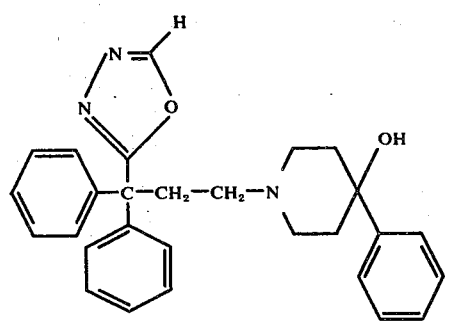

EXAMPLE 10

Using equivalent parts and following the procedure set out in Example 9, 2,2-diphenyl-4-(4-carbethoxy-4-phenyl)piperidinebutyronitrile described in U.S. Pat. No. 3,497,519 is converted to 4-[1,1-diphenyl-3-(4-carbethoxy-4-phenyl)piperidino]propyl-1H-tetrazole. Also according to Example 1, and using equivalent parts, the 1H-tetrazole is converted to 5-[1,1-diphenyl-3-(4-carbethoxy-4-phenyl)-piperidino]propyl-1,3,4-oxadiazole. This compound has the following formula

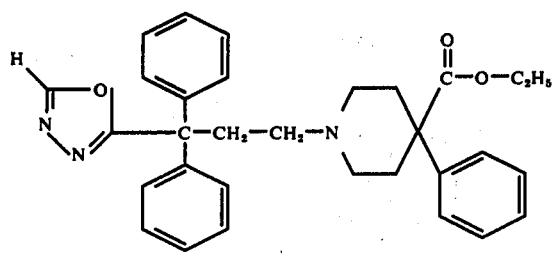

Hydrolysis of 1 part of this ester in 50 parts of methanol containing 15 parts of 20% aqueous sodium hydroxide and isolation provides

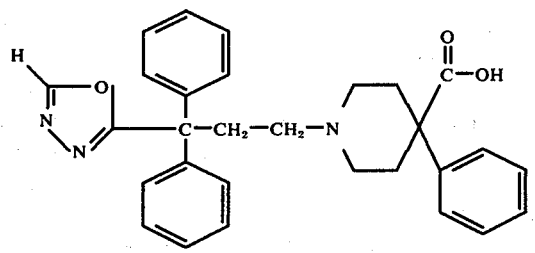

EXAMPLE 11

To solution of 41 parts of α-(4-fluorophenyl)-2-pyridinylacetonitrile (U.S. Pat. No. 3,225,054) in 350 parts of dry toluene is added 9 parts of sodamide and the mixture is stirred and heated at 90° C for 30 minutes. Heating is stopped and a solution of 40 parts of 2-(2-chloroethyl)-2-azabicyclo[2.2.2.]octane in 110 parts of dry toluene is added slowly over a period of 30 minutes. The mixture is stirred and refluxed for 6 hours before it is cooled and decomposed by the addition of water. The toluene layer is separated and washed with water and extracted with 6N hydrochloric acid. The extract is made alkaline and extracted with toluene. The toluene solution is washed with water and dried and the solvent is evaporated. Distillation provides 2-(4-fluorophenyl)-2-(2-pyridyl-4-(2-azabicyclo[2.2.-2]oct-2-yl)butyronitrile. According to the procedure of Example 1 this nitrile is converted to 5-[1-(4-fluorophenyl)-1-(2-pyridyl)-3-(2-azabicyclo[2.2.2]-oct-2-yl)propyl]-1H-tetrazole and in turn to 5-[1-(4-fluorophenyl)-1-(2-pyridyl)-3-(2-azabicyclo[2.2.2.] oct-2-yl)propyl]-1,3,4-oxadiazole having the following structural formula.

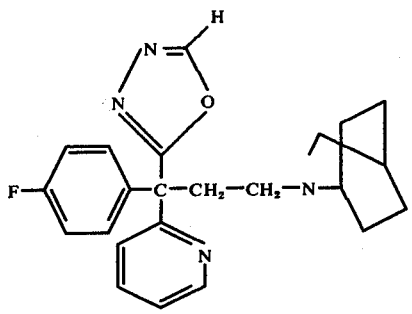

EXAMPLE 12

Initiating reaction sequence in Example 11 with α-(4-chlorophenyl)-4-pyridylacetonitrile provides 5-[1-(4-chlorophenyl)-1-(4-pyridyl)-3-(2-azabicyclo[2.2.-2]oct-2-yl)propyl]-1,3,4-oxadiazole having the following structural formula

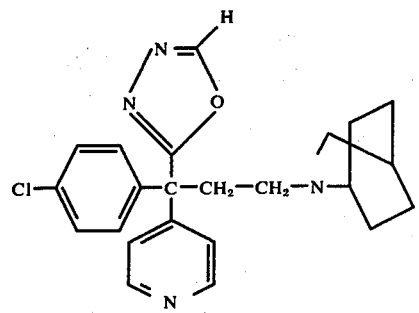

EXAMPLE 13

Initiating the reaction sequence in Example 11 with α-(4-methoxyphenyl)-2-pyridylacetonitrile described in U.S. Pat. No. 3,225,054 provides 5-[1-(4-methoxyphenyl)-1-(2-pyridyl)-3-(azabicyclo[2.2.2]oct-2-yl)propyl]-1,3,4-oxadiazole having the following structural formula

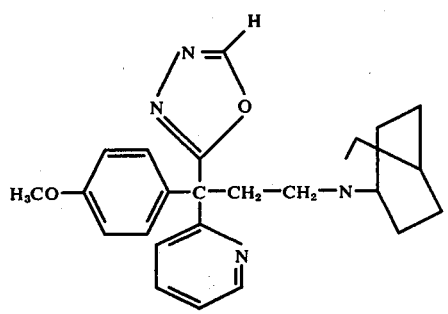

Initiating the reaction sequence in Example 11 with α-(tolyl)-2-(2-pyridyl)acetonitrile described in U.S. Pat. No. 3,225,054 provides 5-[1-(tolyl)-1-(2-pyridyl)-3-(2-azabicyclo[2.2.2]oct-2-yl)propyl]-1,3,4-oxadiazole having the following structural formula

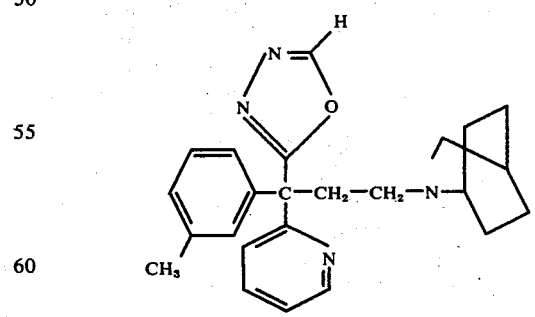

EXAMPLE 14

Following the procedure set out in Example 2 using equivalent quantities and replacing 2-(2-chloroethyl)-2-azabicyclo[2.2.2]octane with 3-(3-chloropropyl)-3- azabicyclo[3.2.2]nonane (U.S. Pat. No. 3,318,869) provides 2-phenyl-2-(3-pyridyl)-5-(3-azabicyclo[3.2.2]non-3-yl)valeronitrile which is converted to 5-[1-phenyl-1-(3-phenyl-1-(3-pyridyl)-4-(3-azabicyclo[3.2.2]non-3-yl)butyl]-1H-tetrazole which in turn is converted to 5-[1-phenyl-1-(3-pyridyl)-4-(3-azabicyclo[3.2.2]non-3-yl)butyl]-2-methyl-1,3,4-oxadiazole, having the following structural formula

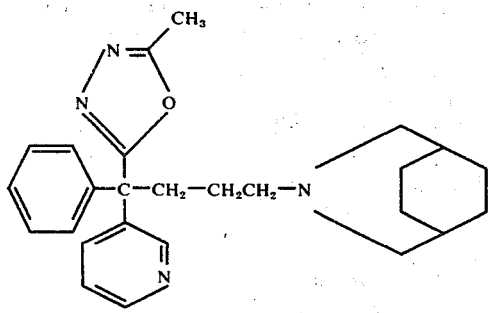

EXAMPLE 15

Following the procedures in Example 2 using 5-[1-phenyl-1-(4-pyridyl)-3-(2-azabicyclo[2.2.2]oct-2-yl)propyl]-1H-tetrazole (Example 5) and replacing acetic anhydride with propionic anhydride provides 5-[1-phenyl-1-(4-pyridyl)-3-(2-azabicyclo[2.2.2]oct-2-yl)propyl]-2-ethyl-1,3,4-oxadiazole, having the following structural formula

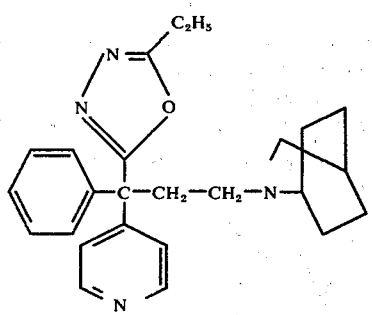

EXAMPLE 16

Initiating the reaction sequence in Example 2 with p-chlorobenzyl cyanide and using equivalent quantities of all other reactants provides 5-[1-(p-chlorophenyl)-1-(3-pyridyl)-3-(2-azabicyclo[2.2.2]oct-2-yl)propyl]-2-methyl-1,3,4-oxadiazole, having the following structural formula

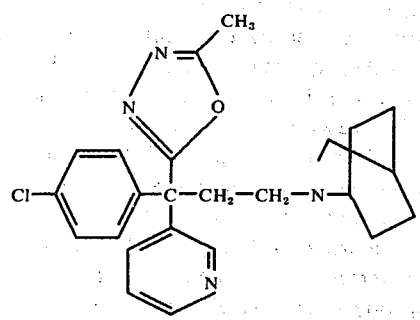

EXAMPLE 17

Initiating the reaction sequence in Example 2 with p-fluorobenzyl cyanide and using equivalent quantities of all other reactants provides 5-[1-(p-fluorophenyl)-1-(3-pyridyl)-3-(2-azabicyclo[2.2.2]oct-2-yl)propyl]-2-methyl-1,3,4-oxadiazole, having the following structural formula

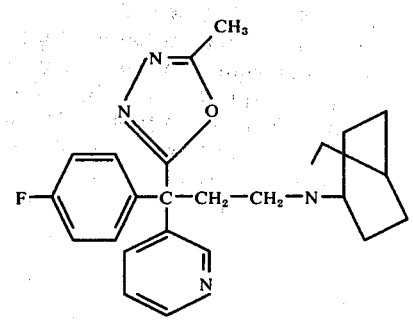

EXAMPLE 18

Initiating the reaction sequence in Example 2 with p-methoxybenzyl cyanide and using equivalent quantities of all other reactants provides 5-[1-(p-methoxyphenyl)-1-(3-pyridyl)-3-(2-azabicyclo[2.2.2]oct-2-yl)propyl]-2-methyl-1,3,4-oxadiazole, having the following structural formula

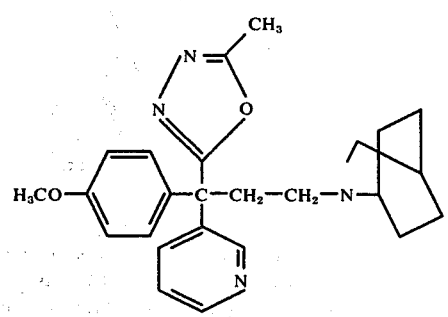

EXAMPLE 19

Following the procedure in Example 2 and replacing 2-(2-chloroethyl)-2-azabicyclo[2.2.2]octane with 6-(2-chloroethyl)-6-azabicyclo[3.2.1]octane provides 5-[1-phenyl-1-(3-pyridyl)-3-(6-azabicyclo[3.2.1]oct-6-yl)propyl]-2-methyl-1,3,4-oxadiazole, having the following structural formula

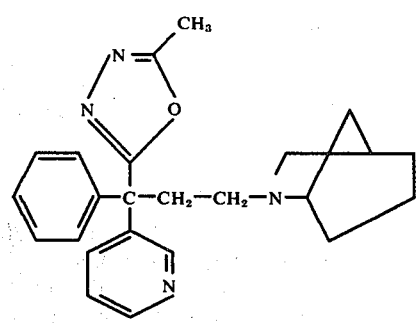

EXAMPLE 20

To a stirred suspension of 7 parts of sodamide in 90 parts of benzene maintained at 30°-35° C. there is added a solution of α-phenyl-3-pyridylacetonitrile, described in U.S. Pat. No. 3,225,054, in 70 parts of benzene. The mixture is then refluxed for 1 hour, cooled and treated by portionwise addition with one equivalent of the propyl ester of 1-(2-chloroethyl)-4-phenylisonipecotic acid (U.S. Pat. No. 2,898,340) in 45 parts of xylene at 30°-40° C. The resulting mixture is refluxed for 2 hours, cooled, filtered and extracted with dilute hydrochloric acid. The acid extract is rendered alkaline and extracted with ether. The ether extract is treated with gaseous hydrogen chloride to yield the hydrochloride of the propyl ester of 2-(3-pyridyl)-2-phenyl-4(4-carboxy-4-phenyl-1-piperidino)butyronitrile. Following the procedure set out in Example 2 and using equivalent quantities this butyronitrile is converted to 5-[1-phenyl-1-(3-pyridyl)-3-(4-carbpropoxy-4-phenyl)piperidino]propyl-1H-tetrazole which in turn is converted to 5-[1-phenyl-1-(3-pyridyl)-3-(4-carbpropoxy-4-phenyl)piperidino]propyl-2-methyl-1,3,4-oxadiazole, having the following structural formula

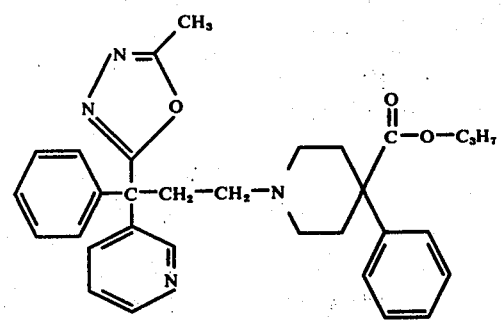

Hydrolysis of 1 part of this ester in 50 parts of methanol containing 15 parts of 20% aqueous sodium hydroxide and isolation provides 5-[1-phenyl-1-(3-pyridyl)-3-(4-carboxy-4-phenyl)piperidino]propyl-2-methyl-1,3,4-oxadiazole, having the following structural formula

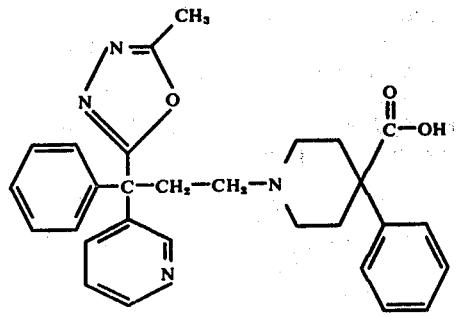

EXAMPLE 21

A solution of 19.3 parts of α-phenyl-3-pyridylacetonitrile in 140 parts by volume of dry benzene is treated with 4 parts of soda amide and the mixture is refluxed with stirring for 1 hour. The mixture is cooled to room temperature and ethylene dichloride 17.2 parts is added. The mixture is stirred and refluxed for 4 hours, cooled, washed with water and dried. Removal of solvent and isolation provides 2-phenyl-2-(3-pyridyl)-4-chlorobutyronitrile. Following the procedure set out in Example 9, 8.9 parts of 4-hydroxy-4-phenylpiperidine are reacted in 400 parts by volume of ethylene glycol monoethyl ether at reflux for 18 hours to provide 2-phenyl-2-(3-pyridyl)-4-(4-hydroxy-4-phenyl)piperidinobutyronitrile. Also following the procedures in Example 9 the latter compound is converted to 5-{1-(phenyl)-1-(3-pyridyl)-3-[4-(4-hydroxy-4-phenyl)piperidino]propyl}-1H-tetrazole and in turn to 5-{1-(phenyl)-1-(3-pyridyl)-3-[4-(4-hydroxy-4-phenyl)piperidino]propyl}-1,3,4-oxadiazole having the following structural formula

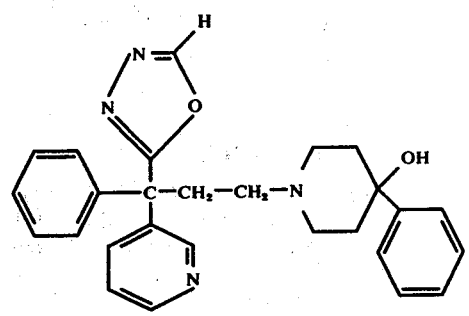

EXAMPLE 22

Following the procedure set out in Example 1 and using equivalent quantities the above tetrazole is converted to 5-{1-(phenyl)-1-(3-pyridyl)-3-[4-(4-hydroxy-4-phenyl)piperidino]propyl}-2-methyl-1,3,4-oxadiazole, having the following structural formula

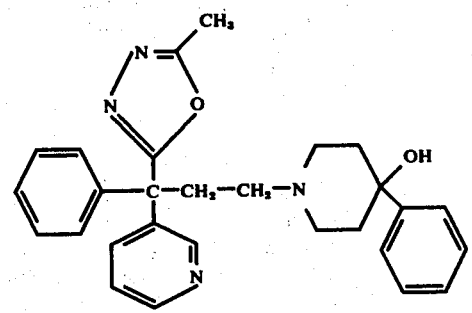

EXAMPLE 23

Following the procedure set out in Example 20 and using equivalent quantities α-phenyl-3-pyridylacetonitrile, described in U.S. Pat. No. 3,225,054 and 2-morpholinoethyl chloride (J. Chem. Soc. pp 505, 1949) provides 2-phenyl-2-(3-pyridyl)-2-morpholinoethylbutyronitrile. Following the procedures set out in Example 1 this nitrile is converted to 5-[1-phenyl-1-(3-pyridyl)-3-(morpholino) propyl]-1H-tetrazole which in turn is converted to 5-[1-phenyl-1-(3-pyridyl)-3-(morpholino)propyl]-1,3,4-oxadiazole, having the following structural formula

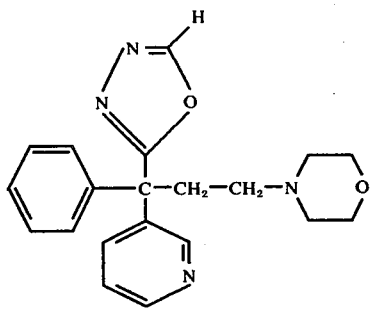

The above tetrazole is reacted with acetic anhydride by the procedures set out in Example 2 using equivalent quantities to provide 4-[1-(phenyl)-1-(3-pyridyl)-3-(morpholino)propyl]-2-methyl-1,3,4-oxadiazole having the following structural formula

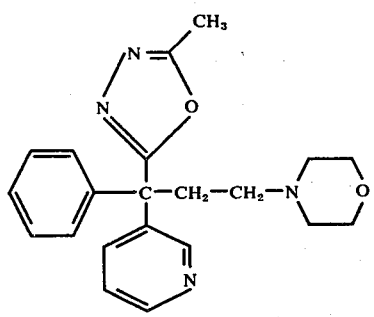

What is claimed is:
1. A compound of the formula

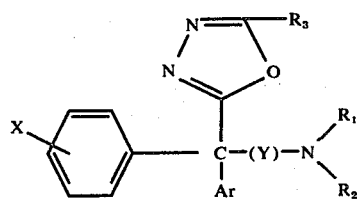

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula

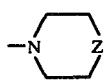

wherein Z is oxygen, methylene, phenylhydroxymethylene, phenylcarboxymethylene, phenylloweralkoxymethylene, or an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms, or loweralkoxy having 1–7 carbon atoms when $R_3$ is hydrogen, or Ar is 3 or 4 pyridyl when $R_3$ is lower alkyl having 1–7 carbon atoms.

2. A compound according to claim 1 of the formula

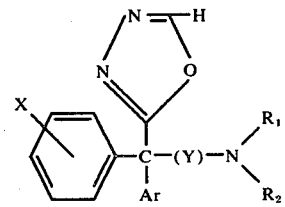

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula

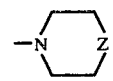

wherein Z is oxygen, methylene, phenylhydroxymethylene, phenylcarboxymethylene, phenylloweralkoxymethylene, or an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms or loweralkoxy having 1–7 carbon atoms.

3. A compound according to claim 1 of the formula

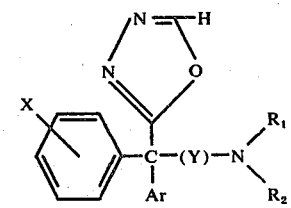

and the pharmaceutically acceptable acid addition salts thereof wherein Y is alkylene having 1–4 carbon atoms; $R_1$ and $R_2$ together with N is a heterocyclic ring system consisting of an azamonocyclic ring of the formula

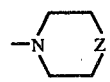

wherein Z is oxygen, methylene, phenylhydroxymethylene, phenylcarboxymethylene, phenylloweralkoxymethylene, X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms, or loweralkoxy having 1–7 carbon atoms.

4. A compound according to claim 1 of the formula

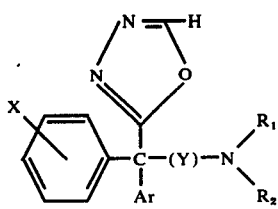

and the pharmaceutically acceptable acid addition salts thereof wherein Y is alkylene having 1–4 carbon atoms; R₁ and R₂ together with N is a heterocyclic ring system consisting of an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; and Ar is phenyl, pyridyl, or monosubstituted phenyl wherein the substituent is halogen, loweralkyl having 1–7 carbon atoms, or loweralkoxy having 1–7 carbon atoms.

5. A compound according to claim 1 of the formula

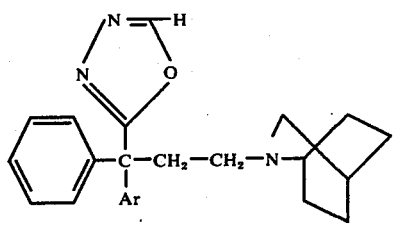

and the pharmaceutically acceptable acid addition salts thereof wherein Ar is phenyl or pyridyl.

6. A compound according to claim 1 which is 5-[1,1-diphenyl-3-(2-azabicyclo[2.2.2]oct-2-yl)propyl]-1,3,4-oxadiazole.

7. A compound according to claim 1 of the formula

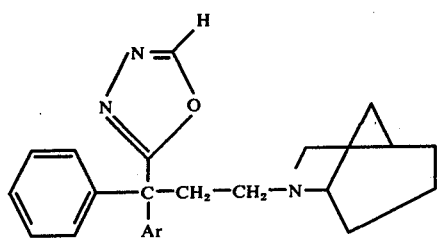

and the pharmaceutically acceptable acid addition salts thereof wherein Ar is phenyl or pyridal.

8. A compound according to claim 1 of the formula

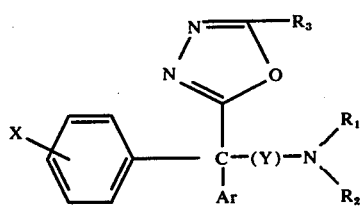

and the pharmaceutically acceptable acid addition salts thereof wherein Y is alkylene having 1–4 carbon atoms; R₁ and R₂ together with N is a heterocyclic ring system consisting of an azamonocyclic ring of the formula

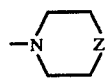

wherein Z is oxygen, methylene, phenylhydroxymethylene, phenylcarboxymethylene, phenylloweralkoxymethylene, or an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; Ar is 3 or 4 pyridyl; and R₃ is lower alkyl having 1–7 carbon atoms.

9. A compound according to claim 1 of the formula

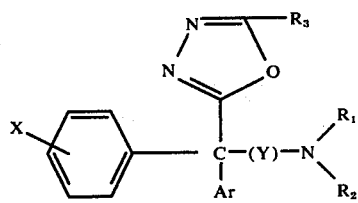

and the pharmaceutically acceptable acid addition salts thereof wherein Y is alkylene having 1–4 carbon atoms; R₁ and R₂ together with N is a heterocyclic ring system consisting of an azamonocyclic ring of the formula

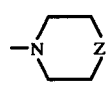

wherein Z is oxygen, methylene, phenylhydroxymethylene, phenylcarboxymethylene, or phenylloweralkoxymethylene; X is hydrogen, halogen, loweralkyl having 1–7 carbon atoms, or loweralkoxy having 1–7 carbon atoms; Ar is 3 or 4 pyridyl; and R₃ is lower alkyl having 1–7 carbon atoms.

10. A compound according to claim 1 of the formula

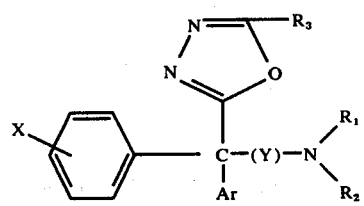

and the pharmaceutically acceptable acid addition salts thereof wherein Y is alkylene having 1–4 carbon atoms; R₁ and R₂ together with N is a heterocyclic ring system consisting of an azabicycloalkane structure having 6–9 carbon atoms and having at least 5 atoms in each ring of the azabicycloalkane structure; X is hydrogen, halogen, loweralkyl having 1–7 carbon atoms, or loweralkoxy having 1–7 carbon atoms; Ar is 3 or 4 pyridyl; and R₃ is lower alkyl having 1–7 carbon atoms.

11. A compound according to claim 1 of the formula

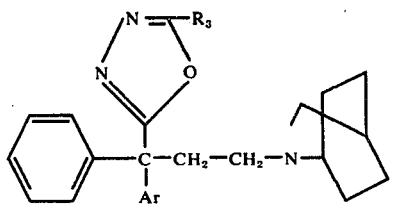

and the pharmaceuticaly acceptable acid addition salts thereof wherein Ar is 3 or 4 pyridyl and $R_3$ is lower alkyl having 1–7 carbon atoms.

12. A compound according to claim 1 which is 5-[1-phenyl-1-(4-pyridyl)-3-(2-azabicyclo[2.2.2]oct-2-yl)propyl]-2-methyl-1,3,4-oxadiazole.

13. A compound according to claim 1 which is 5-[1-phenyl-1-(3-pyridyl)-3-(2-azabicyclo[2.2.2]oct-2-yl)propyl]-2-methyl-1,3,4-oxadiazole.

14. A compound according to claim 1 which is

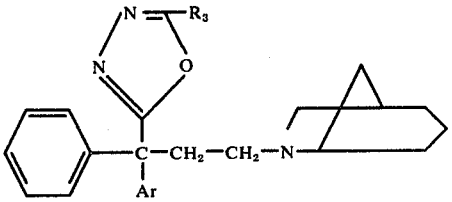

and the pharmaceutically acceptable acid addition salts thereof wherein Ar is 3 or 4 pyridyl and $R_3$ is lower alkyl having 1–7 carbon atoms.

15. A compound according to claim 1 which is 5-[1-phenyl-1-(3-pyridyl)-3-(6-azabicyclo[3.2.1]oct-6-yl)propyl]-2-methyl-1,3,4-oxadiazole.

* * * * *